United States Patent [19]
Shih et al.

[11] Patent Number: 5,373,734
[45] Date of Patent: Dec. 20, 1994

[54] METHOD AND APPARATUS FOR DETERMINING THE QUALITY OF A COATING

[75] Inventors: Hong Shih, West Covina; Manuel S. Mekhjian, Fremont, both of Calif.

[73] Assignee: FMC Corporation, Chicago, Ill.

[21] Appl. No.: 126,831

[22] Filed: Sep. 24, 1993

[51] Int. Cl.⁵ ............................................. G01N 27/02
[52] U.S. Cl. ...................................... 73/150 R; 324/439; 204/434; 204/412; 427/8
[58] Field of Search .............. 73/150 R; 324/439, 693, 324/716; 427/8; 204/434, 412

[56] References Cited

U.S. PATENT DOCUMENTS

| | | | |
|---|---|---|---|
| 4,182,638 | 1/1980 | Cooke | 427/8 |
| 4,256,542 | 3/1981 | Tytgat et al. | 204/412 |
| 4,840,719 | 6/1989 | Jasinski | 204/404 |
| 4,894,251 | 1/1990 | Sieverin | 427/8 |
| 5,217,594 | 6/1993 | Henkens et al. | 204/412 |

FOREIGN PATENT DOCUMENTS 0152500 9/1982 Japan ........................... 204/434

OTHER PUBLICATIONS

Abstract of JA 149049, published Nov. 1980.

Primary Examiner—Diego F. F. Gutierrez
Attorney, Agent, or Firm—Michael Lee; R. C. Kamp; R. B. Megley

[57] ABSTRACT

A method and apparatus for measuring the quality of a coating on a plate. The invention uses a method of measuring the impedance of a coating on a plate, which uses the steps of placing the coating on a plate in a chamber, and then placing a counter electrode in the chamber so that the coating lies between the plate and the counter electrode. A reference electrode is placed in the chamber so that the coating lies between the reference electrode and the plate, and the chamber is filled with a fluid with an ionic substrate. A potentiostat induces a voltage between the plate and the reference electrode, and the impedance of the coating is measured to determine the quality of the coating.

5 Claims, 2 Drawing Sheets

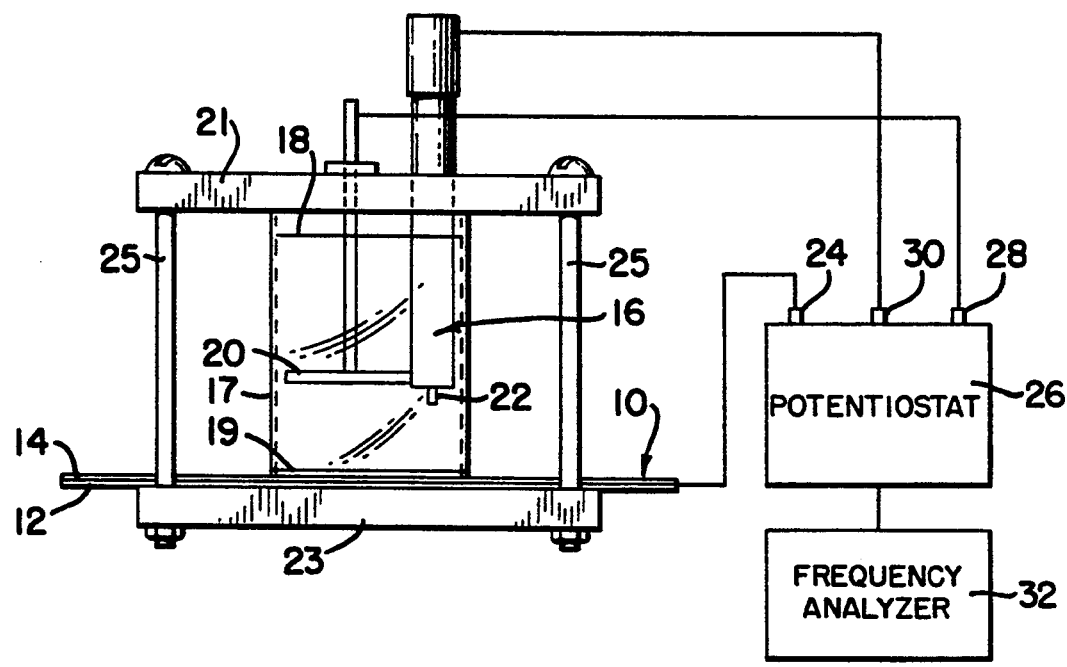
FIG_1
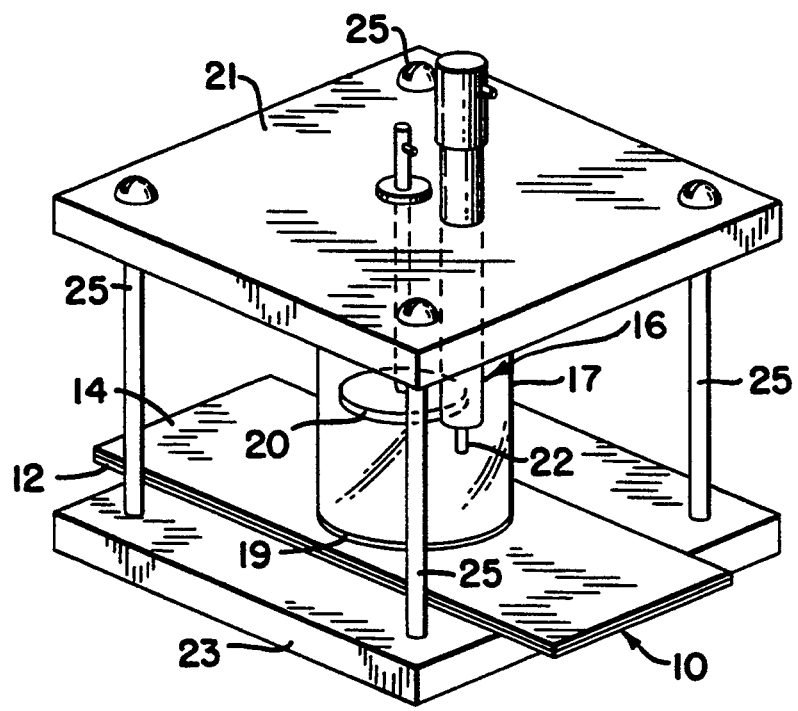
FIG_2

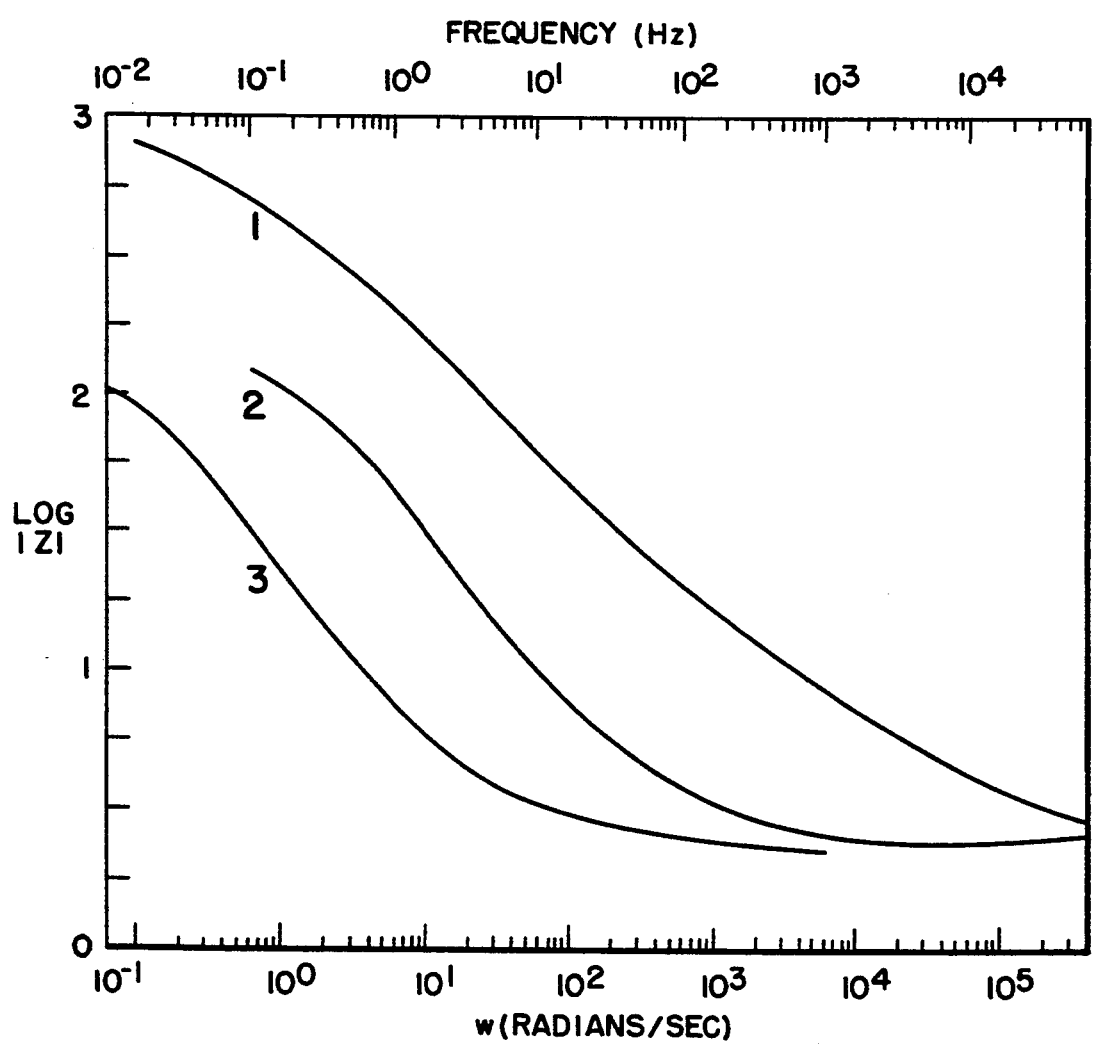
FIG_3

METHOD AND APPARATUS FOR DETERMINING THE QUALITY OF A COATING

In the prior art testing of certain coatings, such as phosphate coatings on metal, a salt spray test is used. Such salt spray tests take twenty four hours.

A goal of the invention is to provide a quick test for testing coatings.

The invention provides an electrochemical impedance spectroscopy test for testing coatings.

BRIEF DESCRIPTION OF THE DRAWINGS

FIG. 1 is a schematic side and elevation of a coating impedance measuring device.

FIG. 2 is a perspective view of the coating impedance measuring chamber, illustrated in FIG. 1.

FIG. 3 is a bode impedance plot of three groups of phosphate coatings, plotting impedance against frequency.

DETAILED DESCRIPTION OF THE DRAWINGS

FIGS. 1 and 2 show a coated plate 10. The coated plate 10 comprises a plate of conducting material 12, with a coating 14, which is to be tested. The coating 14 to be tested may be of various materials such as phosphate or chromate.

The coated plate 10 is placed in a chamber 16 containing a fluid 18 with an ionic substrate. In this embodiment, the chamber is formed by a cylindrical wall 17 held against the plate 10, with a seal between the cylindrical wall 17 and the plate being provided by an O-ring 19, so that the plate 10 forms the bottom of the chamber 16. A top piece 21 forms a cover and a top support for the chamber 16. A bottom piece 23 forms a bottom support for the chamber 16 and the plate 10. The top piece 21 and the bottom piece 23 are mechanically connected by bolts 25. A counter electrode 20 is formed by a large plate within the fluid 18 within the chamber 16. A reference electrode 22 is also placed in the fluid 18, within the chamber 16.

The plate of conducting material 12 is electrically connected to a working electrode terminal 24 of a potentiostat 26. The counter electrode 20 is electrically connected to a counter electrode terminal 28 of the potentiostat 26. The reference electrode 22 is electrically connected to a reference electrode terminal 30 of the potentiostat 26.

In operation, a coated plate 10 with a coating 14 to be tested was placed in the chamber 16 and electrically connected to the working electrode terminal 24 of the potentiostat 26. The coated plate 10 was placed in a position so that the coating 14 was between the plate of conducting material 12 and the counter electrode 20 and the reference electrode 22, and so that the coated plate 10 was substantially parallel to the counter electrode 20 as shown. The potentiostat 26 applied an a.c. signal of 10 mv amplitude between the working electrode terminal 24 and the reference electrode terminal 30, at a frequency of 1 Hertz. The frequency of the voltage signal was controlled by a frequency response analyzer 32. The impedance was calculated from the applied voltage signal and current response using the equation $Z=V/I$, where $Z$ is the impedance, $V$ is the applied voltage and $I$ is the current response. If the impedance was below 20 ohms then the coating was determined to be a poor coating.

In other embodiments other frequencies in the range of 0.1 to 100 Hertz may be used. Other embodiments may use frequencies up to 10,000 Hertz.

FIG. 3 is a bode impedance plot of three groups of phosphate coatings, plotting impedance against frequency over a frequency range from 0.1 Hz to 65,000 Hz. The logarithm of the impedance is plotted along the vertical axis and the frequency is plotted along the horizontal axis on a logarithm scale. At 1 Hz, coating 1 had an impedance of 205 ohms, and coating 2 had an impedance of 80 ohms, and coating 3 had an impedance of 8 ohms. From this test, coating 3 was designated as a poor coating, while coating 1 was designated as high quality coating and coating 2 was designated as a sufficient coating.

A more automated machine electrically connected to the potentiostat would provide an automatic display indicating a good or poor coating for a specified impedance threshold.

In other embodiments, a cylinder wall and a chamber bottom may form a chamber. Holding brackets instead of the edges of the cylinder walls may then be used to hold a coated plate in a position parallel to a counter electrode.

While a preferred embodiment of the present invention has been shown and described herein, it will be appreciated that various changes and modifications may be made therein without departing from the spirit of the invention as defined by the scope of the appended claims.

What is claimed is:

1. A method of determining the quality of a coating on a plate, comprising the steps of:
    placing the coating on a plate; placing the coated plate in a chamber;
    placing a counter electrode in the chamber so that the coating lies between the plate and the counter electrode;
    placing a reference electrode in the chamber so that the coating lies between the reference electrode and the plate;
    filling the chamber with a fluid with an ionic substrate;
    electrically connecting the plate with a working electrode terminal of a potentiostat;
    electrically connecting the counter electrode with a counter electrode terminal of the potentiostat;
    electrically connecting the reference electrode with a reference electrode terminal of the potentiostat
    measuring the impedance between the reference electrode and the plate; and
    determining from the measured impedance the quality of the coating.

2. The method, as claimed in claim 1, wherein the impedance is measured at a potentiostat's frequency between 0.1 and 10,000 Hertz.

3. The method, as claimed in claim 1, wherein the impedance is measured at a potentionstat's frequency between 0.1 and 100 Hertz.

4. The method, as claimed in claim 3, wherein the counter electrode is formed by a second plate and is placed substantially parallel to the coated plate.

5. The method, as claimed in claim 4, wherein the impedance is measured at a potentionstat's frequency of 1 Hertz.

* * * * *